(12) United States Patent
Bensimon et al.

(10) Patent No.: US 9,738,924 B2
(45) Date of Patent: Aug. 22, 2017

(54) METHOD OF DNA DETECTION AND QUANTIFICATION BY SINGLE-MOLECULE HYBRIDIZATION AND MANIPULATION

(71) Applicants: CENTRE NATIONAL DE LA RECHERCHE SCIENTIFIQUE (CNRS), Paris (FR); ECOLE NORMALE SUPERIEURE, Paris (FR); UNIVERSITE PIERRE ET MARIE CURIE (Paris 6), Paris (FR)

(72) Inventors: David Bensimon, Paris (FR); Jean-Francois Allemand, Bourg la Reine (FR); Fang-Yuan Ding, Alhambra (CA); Vincent Croquette, Antony (FR)

(73) Assignees: CENTRE NATIONAL DE LA RECHERCHE SCIENTIFIQUE (CNRS), Paris (FR); ECOLE NORMALE SUPERIEURE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 350 days.

(21) Appl. No.: 14/367,325

(22) PCT Filed: Dec. 21, 2012

(86) PCT No.: PCT/EP2012/076644
§ 371 (c)(1),
(2) Date: Jul. 1, 2014

(87) PCT Pub. No.: WO2013/093005
PCT Pub. Date: Jun. 27, 2013

(65) Prior Publication Data
US 2015/0031028 A1    Jan. 29, 2015

(30) Foreign Application Priority Data

Dec. 22, 2011  (EP) ..................................... 11306743

(51) Int. Cl.
*C12Q 1/68*     (2006.01)
*C12P 19/34*    (2006.01)
(Continued)

(52) U.S. Cl.
CPC ......... *C12Q 1/6825* (2013.01); *C12Q 1/6816* (2013.01); *C12Q 1/6883* (2013.01);
(Continued)

(58) Field of Classification Search
USPC ......... 435/6.1, 6.11, 91.1, 183; 436/94, 501; 536/23.1, 24.3
See application file for complete search history.

(56) References Cited

U.S. PATENT DOCUMENTS 5,705,365 A   1/1998  Ryder et al.
5,840,487 A   11/1998  Nadeau et al.
(Continued)

FOREIGN PATENT DOCUMENTS

EP    329 198    8/1989
WO    92/16659   10/1992
(Continued)

OTHER PUBLICATIONS

International Search Report received in PCT/EP2012/076644, mailed Apr. 8, 2013.
(Continued)

*Primary Examiner* — Frank Lu
(74) *Attorney, Agent, or Firm* — Arrigo, Lee & Guttman LLP (57) ABSTRACT

The present invention relates to a fast method for the detection and the quantification of a nucleic acid, DNA or RNA. Specifically, the invention provides a method for detecting and quantifying the presence of a specific nucleic acid molecule which is based on physical and electronic treatments. The method of the invention is particularly (Continued)

useful for applications as diverse as detection of chromosomal abnormal distributions or gene expression analysis.

15 Claims, 5 Drawing Sheets

(51) Int. Cl.
    *C07H 21/02*      (2006.01)
    *C07H 21/04*      (2006.01)

(52) U.S. Cl.
    CPC ..... *C12Q 1/6886* (2013.01); *C12Q 2525/301* (2013.01); *C12Q 2600/156* (2013.01)

(56) References Cited

U.S. PATENT DOCUMENTS

| | | |
|---|---|---|
| 5,858,658 A | 1/1999 | Haemmerle et al. |
| 6,453,245 B1 | 9/2002 | Rothberg et al. |
| 7,919,247 B2 | 4/2011 | Stuyver et al. |
| 2006/0292608 A1 | 12/2006 | Pinkel et al. |
| 2011/0033855 A1 | 2/2011 | Hori et al. |

FOREIGN PATENT DOCUMENTS

| | | |
|---|---|---|
| WO | 02/31463 | 4/2002 |
| WO | 2006/058395 | 6/2006 |
| WO | 2011147931 A1 | 12/2011 |

OTHER PUBLICATIONS

Piercen M. Oliver et al., Quantitative High-Resolutoin Sensing of DNA Hybridization Using Magnetic Tweezers with Evanescent Ilimunation, vol. 3, No. 2, Jan. 1, 2011, p. 581, XP055028372.

Chiu Rossa W K et al, "Non-invasive prenatal diagnosis by single molecule counting technologies" Trends in Genetics, vol. 25, No. 7. Jul. 2009 (Jul. 2009) pp. 324-331. XP026301457.

Nelson Bryce P et al: "Label-free detection of 16S ribosomal RNA hybridization on reusable DNA arrays using surface plasmon resonance imaging", Environmental Microbiology. Blackwell Science. Oxford. GB, vol. 1 . 4, No. 11, Nov. 1, 2002 (Nov. 1, 2002), pp. 735-743. XP002245180.

Eguchi Keisuke et al, "Oligo(dT)-immobilized pipette tip: Efficient new methodology for mRNA preparation and direct gene amplification", Clinical Chemistry, vol. 44, No. 10 Oct. 1998 (Oct. 1998), pp. 2208-2210, XP002677390.

Bianchi et al. "Isolation of fetal DNA from nucleated erythrocytes in maternal blood" (1990) Proc. Natl. Acad. Sci. USA, vol. 87, pp. 3279-3283.

Brower-Toland et al. "Mechanical disruption of individual nucleosomes reveals a reversible multistage release of DNA" PNAS (2002) vol. 99 No. 4 pp. 1960-1965.

Buehler et al. "Rapid quantification of DNA libraries for next-generation sequencing", Methods, (2010) vol. 50, pp. 15-18.

Chiu et al. "Non-invasive prenatal assessment of trisomy 21 by multiplexed maternal plasma DNA sequencing: large scale validity study", BMJ (2011) vol. 342 pp. 1-9.

Clark et al. "An Oligonucleotide Fingerprint Normalized and Expressed Sequence Tag Characterized Zebrafish cDNA Library", Genome Research (2001) vol. 11 pp. 1594-1602.

Essevaz-Roulet et al. "Mechanical separation of the complementary strands of DNA", Proc. Natl. Acad. Sci. USA (1997) vol. 94 pp. 11935-11940.

Fan et al. "Noninvasive diagnosis of fetal aneuploidy by shotgun sequencing DNA from maternal blood", PNAS (2008) vol. 105 No. 42 pp. 16266-16271.

Gosse et al. "Magnetic Tweezers: Micromanipulation and Force Measurement at the Molecular Level", Biophysical Journal (2002) vol. 82 pp. 3314-3329.

Hague et al. "Performance of high-throughput DNA quantification methods", BMC Biotechnology (2003) vol. 3 pp. 1-10.

Herzenberg et al. "Fetal cells in the blood of pregnant women: Detection and enrichment by fluorescence-activated cell sorting", Proc. Natl. Acad. Sci. (1979) vol. 76. No. 3, pp. 1453-1455.

Lo et al. "Quantitative Analysis of Fetal DNA in Maternal Plasma and Serum: Implications for Noninvasive Prenatal Diagnosis", Am. J. Hum. Genet. (1998) vol. 62, pp. 768-775.

Lo "Quantitative Analysis of Fetal DNA in Maternal Plasma and Serum: Implications for Noninvasive Prenatal Diagnosis", BJOG An International Journal of Obstetrics and Gynaecology (2009) vol. 116, pp. 152-157.

Piepenburg et al. "DNA Detection Using Recombination Proteins", PLoS Biology (2006) vol. 4 Issue 7, pp. 1115-1121.

Stick et al. "The Elasticity of a Single Supercoiled DNA Molecule", Science (1996) vol. 271 pp. 1835-1837.

Turner et al. "Regulation of the Bacillus subtilis Pyrimidine Biosynthetic (pyr) Gene Cluster by an Autogenous Transcriptional Attenuation Mechanism", Journal of Bacteriology (1994) pp. 3708-3722.

Van der Meide "Quantitative Nucleic Acid Sequence-Based Assay as a New Molecular Tool for Detection and Quantification of Leishmania Parasites in Skin Biopsy Samples", Journal of Clinical Microbiology (2005) vol. 43 No. 11, pp. 5560-5566.

Verjat et al. "Multiparametric duplex real-time nucleic acid sequence-based amplification assay for mRNA profiling", BioTechniques (2004) vol. 37, pp. 476-481.

Vernon et al. "Bioelectronic DNA detection of human papillomaviruses using eSensor™: a model system for detection of multiple pathogens", BMC Infectious Diseases (2003) vol. 3 No. 12 pp. 1-9.

Vural "Quantification and presence of human ancient DNA in burial place remains of Turkey using real time polymerase chain reaction" African Journal of Biotechnology (2009), vol. 8, pp. 5163-5168.

Weston et al. "The Metal Homeostasis Protein, Lsp, of *Streptococcus pyogenes* Is Necessary for Acquisition of Zinc and Virulence†", Infection and Immunity (2009) vol. 77, No. 7, pp. 2840-2848.

Woodside et al. "Nanomechanical measurements of the sequence-dependent folding landscapes of single nucleic acid hairpins" PNAS (2006) vol. 103 No. 16, pp. 6190-6195.

Zhang et al. "The catalase-peroxidase gene and isoniazid resistance of Mycobacterium tuberculosis" Nature (1992) vol. 358, pp. 591-593.

METHOD OF DNA DETECTION AND QUANTIFICATION BY SINGLE-MOLECULE HYBRIDIZATION AND MANIPULATION

CROSS REFERENCE TO RELATED APPLICATIONS

This application is a §371 National Stage Application of PCT/EP2012/076644, filed Dec. 21, 2012, which claims priority to EP 11306743.3, filed Dec. 22, 2011.

BACKGROUND

Field of the Invention

The present invention relates to a fast method for the detection and the quantification of a nucleic acid, DNA or RNA. Specifically, the invention provides a method for detecting and quantifying the presence of a specific nucleic acid molecule which is based on physical and electronic treatments. The method of the invention is particularly useful for applications as diverse as detection of abnormal chromosome distributions or gene expression analysis.

Description of Related Art

The detection and quantification of nucleic acid sequences is of importance for a wide range of commonly utilized biological applications. Applications include the fields of in vitro diagnostics, including clinical diagnostics, research in the fields of molecular biology, high throughput drug screening, veterinary diagnostics, agricultural-genetics testing, environmental testing, food testing, industrial process monitoring and insurance testing. In particular, demonstration of the presence of a specific DNA sequence in a physiological sample constitutes, at the present time, the major line of development of diagnostic methods, e.g. for identifying the probability of bacteria of developing antibiotic resistance, genetic abnormalities, the risks of cancer associated with genetic modifications and viral infections, such as infections associated with HIV or with hepatitis viruses (see for example Zhang et al., *Nature*, 358: 591-593, 1992; Turner et al., *J Bacteriol*, 176(12):3708-3722, 1994; Weston et al., *Infection and Immunity.*, 77(7):2840-2848, 2009). Detection and/or quantification of a particular nucleic acid sequence is also crucial for applications as diverse as prenatal diagnostic, study of gene expression, obtention of ancient DNA, diagnoses of genetic disease, detection of sequence polymorphisms, quantification of DNA repeats, detection of pathogens, identification of genetically-modified organisms etc. (see e.g. WO 02/31463; WO 2006/058395; U.S. Pat. No. 5,705,365; U.S. Pat. No. 5,840,487; U.S. Pat. No. 5,858,658; U.S. Pat. No. 6,453,245; U.S. Pat. No. 7,919,247; Verjat et al., *Biotechniques*, 37(3): 476-481, 2004; Vural, *Afr. J. Biotechnol.*, 8(20): 5163-5168, 2009; van der Meide et al., *J. Clin. Microbiol.*, 43(11): 5560-5566; 2005; Fan et al., *Proc. Natl. Acad. Sci. USA*, 105(42): 16266-16271, 2008; Buehler et al., *Methods*, 50: S15-S18, 2010; Clark et al., *Genome Res.*, 11: 1594-1602, 2001; Vernon et al., *BMC Infect Dis*, 3: 12, 2003; Piepenburg et al., *PLoS Biol.*, 4(7): e204, 2006).

Several techniques have been developed over the years, all relying on the detection of a hybrid molecule between the target nucleic acid molecule and a specific labelled probe. Today, the most widely used methods to detect nucleic acids are based on the polymerase chain reaction (PCR). Real-time PCR for example is used to amplify and simultaneously quantify a targeted DNA molecule.

A crucial aspect in any detection and/or quantification method of nucleic acid is sensitivity. The first techniques developed required large sample sizes. This problem was alleviated by the amplification step in the PCR method. PCR-based methods thus allowed the detection of very small amounts of nucleic acids by amplifying the target nucleic acid (Hague et al., *BMC Biotechnol.*, 3: 20, 2003). In biological research, PCR has thus accelerated the study of testing for communicable diseases. Medical applications of PCR include identifying viruses, bacteria and cancerous cells in human tissues. PCR can even be used within single cells, in a procedure called in situ (in-site) PCR, to identify specific cell types. PCR can also be applied to the amplification of RNA, a process referred to as reverse transcriptase PCR (RT-PCR). RT-PCR is similar to regular PCR, with the addition of an initial step in which DNA is synthesized from the RNA target using an enzyme called a reverse transcriptase. A wide variety of RNA molecules have been used in RT-PCR, including ribosomal RNA, messenger RNA and genomic viral RNA.

However, all the methods developed so far suffer from serious drawbacks. In particular, they all make use of labeled nucleotides (e.g. labeled with fluorescence), thus contributing to seriously increasing the overall costs. Moreover, amplification of the target sequence is time consuming, increases the probability of errors, and is highly prone to contamination.

SUMMARY

The method according to the present invention, based on physical techniques and electronic treatments, differs from the current approaches, which are chemical or biochemical. Its advantages are:
1) it does not require a PCR step prior to detection and quantification
2) it does not use expensive labelled nucleotides (either with fluorophores or some other groups).

In addition, the coupling of the method of the invention with a global (electronic or optical) detection of the position of the obstruction along the hairpin allows for fast large scale diagnostics of genomic DNA and provide a competitive alternative to current DNA chip technologies.

The present invention relates to a method for the detection of a nucleic acid sequence, wherein the renaturation of a denatured double stranded nucleic acid corresponding to the said nucleic acid sequence is blocked.

By 'detection of a nucleic acid sequence', it is herein meant all the activities leading directly or indirectly to the obtention of some information on the presence or absence of a specific nucleic acid sequence, including, but not limited to, the detection of a particular sequence in a nucleic acid molecule or the detection of a difference between the sequences of two different nucleic acid molecules. The detection of a nucleic acid sequence may include the actual determination of the sequence of the said nucleic acid, i.e. the deciphering of the actual succession of bases in the said nucleic acid; however, in most embodiments, the invention may be carried out without sequencing the said nucleic acid.

The invention is based on the observation that the two strands of a denatured double-stranded nucleic acid will rehybridize under appropriate conditions. If some molecules are bound to any of the strands of the said denatured double-stranded nucleic acid during the renaturation step, the rehybridization will only be partial. The inventors have now found that, under certain conditions, this pause in rehybridization, permanent or transient, can be used to detect the sequence contained in the denatured double-stranded nucleic acid molecule. According to the invention, it is possible to detect a blockage of the rehybridization of the double-stranded nucleic acid molecule; the physical parameters (e.g. the duration of the blockage, the position of the blockage on the double-stranded nucleic acid molecule) associated with this blockage then allow the determination of the sequence of the nucleic acid.

The present invention thus relates to a method for the detection of a nucleic acid sequence, said method comprising a step of detecting a blockage of the renaturation of a denatured double stranded nucleic acid corresponding to the said nucleic acid sequence.

By 'denaturation', it is herein meant the process of separation of the two strands of a double-stranded nucleic acid molecule occurring when most of the hydrogen bonds between the said strands are broken. The denaturation process yields a denatured nucleic acid molecule, by which it is herein meant the two separated complementary strands resulting from the denaturation of a double-stranded nucleic acid molecule. By 'renaturation', it is herein referred to the process by which two separated complementary strands reform through hybridization into a double helix. As used herein, 'hybridization' is the process of establishing a non-covalent, sequence-specific interaction between two or more complementary strands of nucleic acids into a single hybrid.

There are several possibilities known to the skilled person to denature the nucleic acid. In a most preferred manner, the two strands are separated by submitting them to a physical force. For example, the free ends of the said double-stranded nucleic acid may be pulled apart, thus rupturing all the bonds between the paired bases, and opening the double-stranded nucleic acid.

BRIEF DESCRIPTION OF THE DRAWINGS

FIGS. 1-5 represents embodiments described herein.

DETAILED DESCRIPTION OF A PREFERRED EMBODIMENT

Thus, in one embodiment, the method of the invention relates to a method for the detection of a nucleic acid sequence, said method comprising the steps of:
  denaturing a double-stranded nucleic acid molecule corresponding to the said nucleic acid sequence by applying a physical force to the said molecule; and
  detecting a blockage of the renaturation of the double-stranded nucleic acid.

In this type of sequence detection method, it can be advantageous, in order to facilitate re-pairing, to arrange for the free ends of the double-stranded DNA (i.e. the ends which are not attached to supports) to be joined to one another covalently or quasi-covalently before pulling apart. In a preferred embodiment; the double-stranded nucleic acid molecule is a hairpin. If it is desired that the double-stranded nucleic acid be represented diagrammatically in the context of the present invention, it is possible to liken it to a "zip fastener", which is opened (or closed): the denaturation of the double-stranded nucleic acid is the unzipping, the renaturation the rezipping.

The inventors have observed that, under certain conditions, when a molecule is bound to the denatured double-stranded nucleic acid molecule, renaturation of the said molecule is blocked. The molecule bound can be of any type of molecule with an affinity for a specific sequence on the said denatured double-stranded nucleic acid molecule, e.g. a nucleic acid, a protein or a small molecule. However, it is preferable to use a single-stranded nucleic acid, since the said single-stranded nucleic acid can hybridize with a complementary sequence on one of the strands of the denatured double-stranded nucleic acid. This single-stranded nucleic acid can be of any length, provided that it is long enough to block the renaturation process. Preferentially, the length of the single stranded nucleic acid will be comprised between 3 and 50 nucleotides; more preferentially, between 3 and 45 nucleotides, between 3 and 40 nucleotides, between 3 and 35 nucleotides, between 3 and 30 nucleotides, between 3 and 25 nucleotides, between 3 and 20 nucleotides, between 3 and 15 and even more preferentially between 3 and 12. The single-stranded nucleic acid of the invention can be in particular a DNA or an RNA molecule, either natural or modified. The said single-stranded nucleic acid may also be made of modified nucleotides, such as locked nucleic acid (LNA), which are nucleotides in which the ribose moiety is modified with an extra bridge connecting the 2' oxygen and 4' carbon, or peptide nucleic acid (PNA), wherein the backbone is composed of repeating N-(2-aminoethyl)-glycine units linked by peptide bonds.

When a single-stranded nucleic acid molecule is added to a denatured double-stranded nucleic acid prior to renaturation, a blockage of rehybridization indicates that the sequence of the single-stranded nucleic acid molecule is complementary to at least part of the sequence of the double-stranded nucleic acid molecule.

Thus, the method of the invention also relates to a method for the detection of a nucleic acid sequence, said method comprising the steps of:
  1) denaturing a double-stranded nucleic acid molecule by applying a physical force to the said molecule;
  2) providing a single-stranded nucleic acid molecule corresponding to the said nucleic acid sequence;
  3) renaturing the said double stranded nucleic acid molecule in the presence of the said single-stranded nucleic acid molecule; and
  4) detecting a blockage of the renaturation of the double-stranded nucleic acid.

The invention applies to any type of double-stranded nucleic acid. Most often, the double-stranded nucleic acid will be DNA, but it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired. Furthermore, the duplex may consist of the at least partial re-pairing of two single strands obtained from samples of different origins. Finally, the invention also applies to the secondary structures of a sole single-stranded DNA or of a sole single-stranded RNA.

In a typical configuration, the double-stranded nucleic acid molecules may be specifically anchored on two solid substrates (e.g. microscope slide, micropipette, microparticle). One of the ends may be attached directly or indirectly to a surface, while the other end is attached directly or indirectly to a movable surface. In this embodiment, a tension is applied on both ends of the double-stranded nucleic acid when the supports are moved away. When the tension is higher than a threshold value, the two strands are separated and the nucleic acid molecule is denatured. The tension applied is preferentially above or equal to 15 pN; it is more preferentially above or equal to 16 pN; it is even more preferentially above or equal to 17 pN; in a very much preferred aspect, it is above or equal to 18 pN. This force may vary with temperature, nucleotide type and buffer, but the skilled person will easily adapt the said force with regard to these parameters in order to obtain the separation of the two strands. On the other hand, when the tension is decreased under a minimal value, the two strands of the denatured double-stranded nucleic acid can rehybridize. To obtain rehybridization of the said two strands, a tension of less than or equal to 12 pN is preferentially applied; more preferentially, it is less than or equal to 11 pN; even more preferentially, it is less than or equal to 10 pN.

Most preferably, the double-stranded nucleic acid is a hairpin. As used herein, 'hairpin' means a double helix wherein the 5' end of one strand is physically linked to the 3' end of the other strand through an unpaired loop. The said physical link can be either covalent or non-covalent. Preferentially, the said physical link is a covalent bond. Thus, a hairpin consists of a double-stranded stem and an unpaired single-stranded loop. In a hairpin, the ends of the two strands which are not engaged in the loop are free and can thus be pulled apart. This results in the unpairing of the double stranded nucleic acid, thus yielding a denatured double stranded nucleic acid molecule. It is possible to open completely a hairpin double-stranded nucleic acid molecule by pulling on each end of the said nucleic acid molecule with a force higher than a threshold value. When the tension applied to the molecule is decreased to less than a minimal value, the nucleic acid molecule rehybridizes to reform a hairpin. The presence of a single-stranded nucleic acid molecule hybridized to one of the nucleic acid strands leads to a pause in rehybridization. Therefore, the detection of such a pause indicates that the single-stranded nucleic acid molecule comprises a sequence which is complementary to at least part of the double-stranded stem.

It is advantageous in this respect to design the loop sequence and length so that the hairpin refolds after a short transient, e.g. 1 second. Methods to this effect have been described in the prior art, e.g. in Woodside et al., *Proc. Natl. Acad. Sci. U.S.A.*, 103 (16): 6190-6195, 2006). When the force is decreased from the opening to the test value, the extension of the open hairpin varies because of the elasticity of single stranded DNA. The small delay before the hairpin refolds allows the user to determine the hairpin extension at the same force than the one used to detect the blocking state.

Using a hairpin makes it possible, in particular, to perform cycles of pairing and unpairing and thus to improve the signal/noise ratio.

Techniques allowing the free ends of double-stranded nucleic acid to be joined together are known, and some will be described in greater details in what follows.

By determination of the blockage, it is herein meant the determination of the physical parameters associated with the blockage. One useful parameter is the position of the blockage on the double-stranded nucleic acid molecule, said position corresponding to the position of hybridization of the single-stranded nucleic acid molecule on the double-stranded nucleic acid molecule. Indeed, the inventors have found that the position on the double-stranded nucleic acid at which the pause in renaturation occurs can be precisely determined: the use of a hairpin affords the skilled person a means to determine the physical distance between the two free ends of the hairpin at any time during the denaturation/renaturation process.

By 'free end' it is herein meant the end of one strand which is not covalently linked to an extremity of the other strand; as explained above, these free ends may each be bound to a different surface. For example, one of these surfaces may be movable; whilst the other may be motionless. The skilled person will thus easily realize that, in order to measure the distance between the free ends of the hairpin double-stranded nucleic acid, it is possible to simply measure the distance between the two surfaces.

Figure 1:
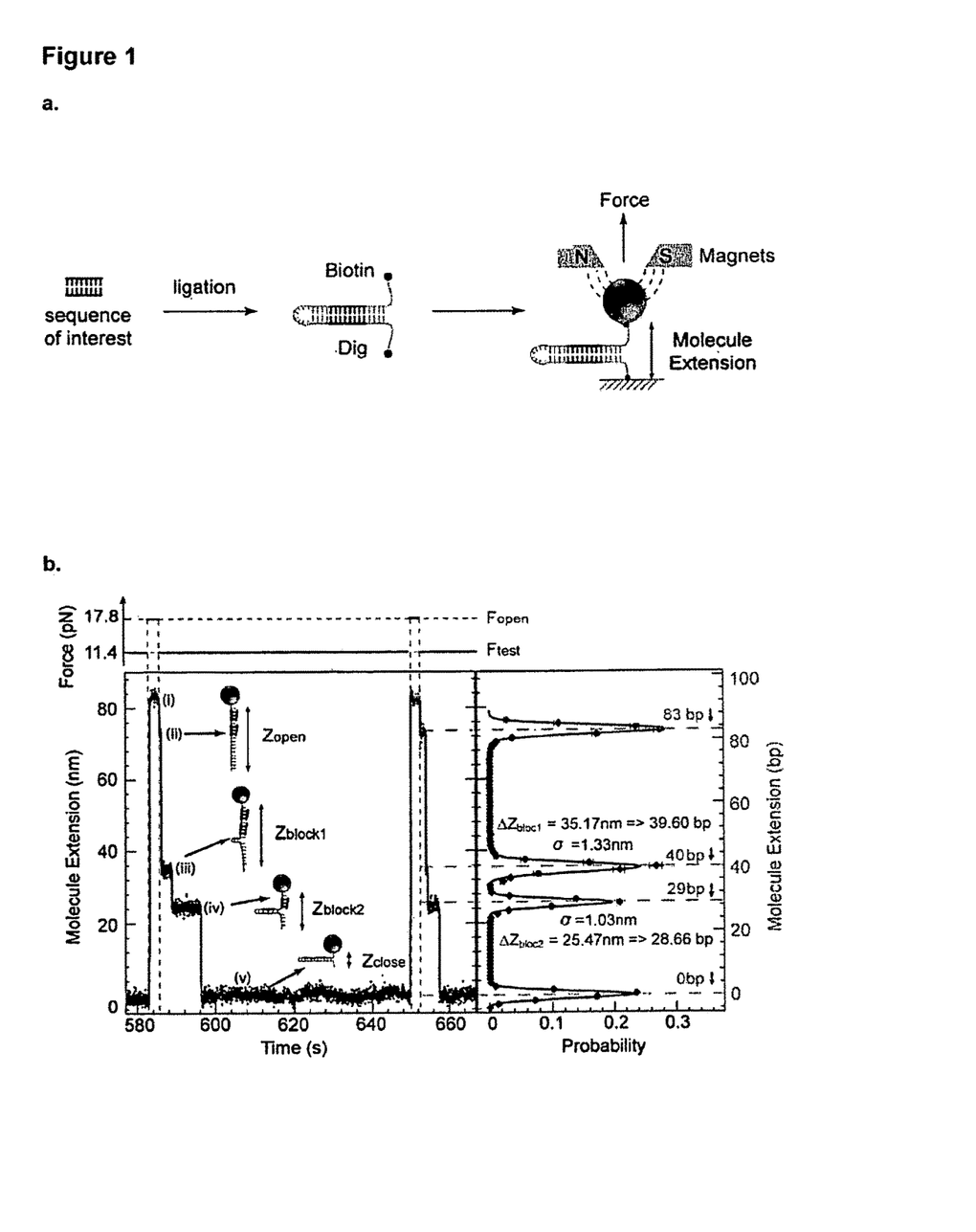

This distance is maximal ($z_{high}$ ($F_{open}$)) when the hairpin molecule is completely denatured, since the hairpin nucleic acid is then completely extended; it is minimal ($z_{low}$ ($F_{test}$)) when the said hairpin molecule is completely renatured. It is advantageous to perform all length comparisons at the same force $F_{test}$, so that the single stranded nucleic acid has the same elastic properties. Using the delay in loop closing the skilled user can measure $z_{high}$ ($F_{test}$). Likewise, the distance between the two free ends when the renaturation process is temporarily paused can be measured: as expected, this distance z is comprised between $z_{high}$ and $z_{low}$ (all z being measured with $F=F_{test}$). It is immediately clear that the distance z varies with the localization in the hairpin molecule of the sequence to which the sequence of the single-stranded nucleic acid is complementary. If the said single-stranded nucleic acid hybridizes with a sequence which is located close to the free ends of the hairpin, the self-rehybridization process is blocked just before the complete hairpin is reformed; in this case, $z_{pause}$ minimal. On the other hand, if the said single-stranded nucleic acid hybridizes with a part of the hairpin which is close to the unpaired loop, the renaturation process will be arrested in a situation where the hairpin is completely, or almost completely denatured; in this case, $z_{pause}$ is maximal (FIG. 1).

In another embodiment, one or more reference single-stranded nucleic acids are hybridized to known sequences on the DNA hairpin (near its base or near its loop for example) and the position of hybridization of the probed single-stranded nucleic acid is measured with respect to the hybridization position of the said reference single-stranded nucleic acids.

It is possible to correlate precisely a physical distance in a double-stranded nucleic acid molecule with a number of bases. For example, a distance of 0.8 nm corresponds to the distance spanned by two nucleotides (1 bp) in a nucleic acid under a 10 pN force. The exact calibration versus force is given by the elasticity of single stranded nucleic acid. Therefore, by simply measuring the distance between the two free ends of the double-stranded nucleic acid molecule (or any two reference positions on the molecule), it is possible to determine precisely where the renaturation is blocked.

Thus, in one embodiment, the invention consists of a method for detecting the sequence of a nucleic acid, wherein the double-stranded nucleic acid molecule corresponding to the sequence to be determined is first denatured by application of a physical force, then rehybridized in a presence of a single-stranded nucleic acid, and the presence of a blockage in the rehybridization detected. In one aspect, the distance between the two ends of the double-stranded molecule is determined when the renaturation process is blocked. Preferentially, the distance between the two ends of the said molecule is determined when the molecule is completely denatured. More preferably, the two distances are compared and the position of the blockage is determined. More preferably, the distance between the fully extended loop and a reference hybridization position is measured and used to determine the position of the blockage. Even more preferentially the distance between two reference hybridization positions is measured and used to determine the position of the blockage.

Aside from its position along the molecule, the most useful parameter associated with the blockage in renaturation is the period of time during which the renaturation is blocked (referred herein as the duration of the pause in renaturation). Indeed, it is possible to measure the period of time during which the rehybridization is blocked. For example, the skilled person can determine the period of time during which the distance between the two ends of the double-stranded nucleic acid is z as defined above, i.e. an intermediate value comprised between $z_{high}$ and $z_{low}$.

The duration of the blockage is dependent upon the degree of complementarity between the two sequences. The higher the complementarity, the greater the number of bonds established between the two molecules, and therefore the longer the duration. It is also clear that the blockage time will be dependent upon the length of the region of complementarity between the two sequences. The longer the region, the greater the number of bonds established between the two molecules, and therefore the longer the duration. It is therefore easily conceivable that under certain conditions the duration of the renaturation pause will be almost permanent. In particular, when the single-stranded nucleic acid comprises more than 20, preferably more than 25, even more preferably more than 30 nucleotides capable of hybridizing with the denatured double-stranded nucleic acid, the single-stranded nucleic acid remains hybridized to the double-stranded hairpin (for many minutes) even when the force applied to the said double-stranded nucleic acid is decreased to $F_{test}$, thus preventing self-rehybridization of the said double-stranded hairpin. In such a case, it may be advantageous to use an enzyme to eject the single-stranded nucleic acid molecule. The ejection of the said single-stranded nucleic acid molecule thus makes it possible to perform cycles of pairing and unpairing and thus improve the signal/noise ratio. As examples of suitable enzymes, one may cite e.g. helicases, including a UvrD helicase, E. coli UvrD helicase, Tte-UvrD helicase, T7 Gp4 helicase, RecBCD helicase, DnaB helicase, MCM helicase, Rep helicase, RecQ helicase, PcrA helicase, T4 UvsW helicase, SV40 large T antigen helicase, Herpes virus helicase, yeast Sgs1 helicase, DEAH_ATP-dependent helicases and Papillomavirus helicase E1 protein and homologs thereof. Preferably, the T4 UvsW helicase is used.

The duration of the pause may also, vary with the conditions of the reaction. Said duration will decrease as the temperature increases. Likewise, the buffer conditions can also modulate the duration of the pause: for example, magnesium, betain and tetramethylammonium chloride (TMAC used at molar concentration) increase the blocking time. These compounds reinforce AT pairs more than GC, thus reducing the difference in strength between these pairs. However, when the temperature and the buffer are fixed, the duration of the pause will only depend on the force pulling on the denatured double-stranded nucleic acid and on its complementarity with the single-stranded nucleic acid.

Thus, in one particular aspect, the method of the invention comprises the steps of:
- denaturing the said double-stranded nucleic acid molecule corresponding to the said nucleic acid sequence by applying a physical force to the said molecule;
- providing a single-stranded nucleic acid molecule,
- renaturing the double-stranded nucleic acid molecule in the presence of the said single-stranded nucleic acid molecule; and
- detecting a blockage of the renaturation of the said double-stranded nucleic acid molecule, and determining the duration of the pause.

Whereas the methods of the prior art all use fluorescent nucleotides, the method of the invention only involves the mechanical detection of the nucleic acid molecule extension. Therefore the method of the invention does not suffer from any of the drawbacks associated with the methods of the prior art.

In a preferred aspect, the detection of the blockage of the renaturation of the said double-stranded nucleic acid molecule involves determining the position of the blockage on the double-stranded nucleic acid molecule, as described above.

In this particular embodiment, the method according to the present invention may be used for diagnostic purposes to permit, in particular, the sequencing of variable regions of nucleic acid corresponding to abnormalities being looked for.

However, it is possible to provide for a simplified technique, based on the observation that a mismatch between the oligonucleotide and the DNA sequence results in a much shorter lived hybridization. In a first aspect, the renaturation of a hairpin double-stranded nucleic acid molecule is blocked by a single-stranded nucleic acid, by any of the methods described above, and the duration of the blockage is determined. In a preferred aspect, this value is compared to a reference value. In a further preferred aspect, the reference value corresponds to the length of the pause observed with a reference single-stranded nucleic acid, as determined by any of the above methods.

For diagnostic purposes, e.g. looking for mutations in genomic DNA, the technique can be implemented in two ways:
1) The hairpins formed with the genomic DNA comprising the sought for mutations are probed with oligonucleotides in solution.
2) The hairpin containing the sequence(s) with the sought-for mutations are probed by the genomic DNA which is present in solution as single-stranded DNA fragments of fixed size. It will be immediately apparent that if the goal of the assay is only to find the existence of a specific sequence or possible mutation in such a sequence, placing this sequence in the loop of the hairpin provides a very simple detection scheme. If the oligo hybridizes in the loop, it completely prevents the refolding of the hairpin leading to a very large extension change, which can thus be easily detected, as described below.

Whereas the methods of the prior art require labelling the probes with fluorescent or radioactive nucleotides, the present method only relies on the mechanical detection of the nucleic acid molecule extension. Moreover, no amplification step prior to detection is required. The method of the present invention thus permits the detection of one single molecule within a whole population of nucleic acid molecules. Because of the single-molecule resolution obtainable with the method of the invention, each molecule carrying a specific sequence can be detected. Thus the present invention affords the skilled person to numerate the number of nucleic acid molecules carrying the said sequence. The present method allows for the easy and accurate quantification of a specific nucleic acid sequence in a whole population of nucleic acid molecules.

It is therefore another aspect of the invention to provide a method for quantifying a species of double-stranded nucleic acid molecules comprising a specific sequence in a sample, the said method comprising the steps of:
a) denaturing the said double-stranded nucleic acid molecules in the sample by applying a physical force to the said molecules;
b) providing a single-stranded nucleic acid molecule corresponding to the said sequence;

c) renaturing the said denatured double-stranded nucleic acid molecules of step a) in the presence of the said single-stranded nucleic acid molecule; and d) detecting the double-stranded nucleic acid molecules where renaturation is blocked; and e) numerating the double-stranded nucleic acid molecules of step d).

The nucleic acid species to be quantified is a population of nucleic acid molecules, which comprise the said specific sequence. They thus differ from other nucleic acid molecules in that they contain this specific sequence. Although these molecules all share this sequence, they may or may not be identical otherwise. In certain embodiments, it may be preferable for the skilled person to measure the quantity of a nucleic acid species which differ outside the said specific sequence; for example, it may be interesting for the skilled person to measure the quantity of both G1 cyclins transcripts CLN1 and CLN2 which are expressed as the budding yeast cells enter the cell cycle. In some other embodiments, it may be more preferable to quantify a population of identical nucleic acid molecules, e.g. different isoforms of a gene resulting from differential splicing. This may be achieved easily by carefully selecting the said specific sequence: the person of skills in the art knows how to design sequences corresponding to one or the other of the above situations with the help of publicly-available sequence databases (e.g. Genbank) and this needs not be further detailed here.

It is also possible to use more than one single strand nucleic acids, said one or more single strand nucleic acids being capable of hybridizing to one or more different sequences along the denatured double stranded nucleic acid molecule.

When more than one single-stranded nucleic acid molecules are used, it is advantageous that the said one or more single strand nucleic acids correspond to one or more distinct sequences. In that case, the said single-stranded nucleic acid molecules may be added simultaneously or sequentially to the denatured double stranded nucleic acid molecule. The said various single-strand nucleic acids can block the renaturation of the said denatured double-stranded nucleic acid at different positions. The number and position of blockages during rehybridization defines a unique fingerprint, based on the extent of similarity of each single-strand nucleic acid sequence to the sequence of the said double-stranded nucleic acid. A fingerprint is thus the pattern of blockages observed as a result of the one or more single strand nucleic acids hybridizing to a double stranded nucleic acid molecule during the renaturation phase of the said denatured double stranded nucleic acid molecule. This fingerprint can be used to identify and numerate various double-stranded molecules in a DNA sample.

The proposed methodology does not require the use of fluorescently labelled probes and provides for additional positional information (beyond the mere hybridization of the probes). For example, using this approach, hundreds of thousands of individual library fragments can be comparatively examined. cDNAs with similar fingerprints are grouped into clusters, and this provides information about the number of expressed genes and their relative expression levels.

Thus, in one specific embodiment, the method of the invention relates to a method for quantifying a species of double-stranded nucleic acid molecules comprising one or more specific sequence in a sample, the said method comprising the steps of:

a) denaturing the said double-stranded nucleic acid molecules in the sample by applying a physical force to the said molecules;

b) providing one or more single-stranded nucleic acid molecule corresponding to the said one or more sequences;

c) renaturing the said denatured double-stranded nucleic acid molecules of step a) in the presence of the said single-stranded nucleic acid molecule;

d) detecting the double-stranded nucleic acid molecules where renaturation is blocked by the said one or more single-stranded nucleic acid molecules; and e) numerating the molecules of step d).

Preferably, at least 2 single-stranded molecules are provided at step b), more preferably, at least 3, still more preferably, at least 5, even more preferably, at least 10, most preferably at least 15.

The sample of the invention is any type of sample which may contain the desired nucleic acid species, such as e.g. a reaction mixture. It may also be, for example, a biological sample. A "biological sample" may be any sample which may contain a biological organism, such as, for example, bacteria, viruses, plants, yeasts etc. A "biological sample" according to the invention also refers to a sample which may be obtained from a biological organism, such as a cellular extract obtained from bacteria, viruses, plants, yeasts etc. in particular, a biological sample may be any sample taken from a subject, such as a serum sample, a plasma sample, a urine sample, a blood sample, a lymph sample, or a biopsy. Such a sample must allow for the quantification of chromosomal sequences. Preferred biological samples for the quantification of genomic sequences include samples such as a blood sample, a plasma sample, a lymph sample, or a biopsy. Preferably, the biological sample is a blood sample. Indeed, such a blood sample may be obtained by a completely harmless blood collection from a pregnant mother and thus allows for e.g. a non-invasive diagnosis of fetal aneuploidy. Also, a blood sample can be used from a cancer patient and, for example, used to characterize a liquid tumor by the method of the invention.

A "biological sample" as used herein also includes a solid cancer sample of the patient to be tested, when the cancer is a solid cancer. Such solid cancer sample allows the skilled person to perform a measurement of the level of the desired nucleic acid by the method of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy. According to one aspect, the sample from the patient is a cancer cell or a cancer tissue.

The sample according to the invention may contain only the nucleic acid species which is to be quantified, but it may also contain other molecules. In a preferred embodiment, the sample contains other species of nucleic acid molecules. According to this embodiment, the invention further relates to a method for quantifying a species of nucleic acid molecules comprising a specific sequence in a sample containing different species of nucleic acid molecules, the said method comprising the steps of:

a) denaturing the double-stranded nucleic acid molecules in the sample by applying a physical force to the said molecules;

b) providing a single-stranded nucleic acid molecule corresponding to the said specific sequence;
c) renaturing the said denatured double-stranded nucleic acid molecules of step a) in the presence of the said single-stranded nucleic acid molecule;
d) detecting the double-stranded nucleic acid molecules where renaturation is blocked; And
e) numerating the double-stranded nucleic acid molecules of step d).

As explained above, it is also possible to use one or more single-stranded nucleic molecules corresponding to one or more sequences, thus allowing the determination of a specific fingerprint. In this embodiment, the method of the invention is based on the quantification of the double-stranded molecules displaying this fingerprint. Thus, according to this embodiment, the invention relates to a method for quantifying a species of nucleic acid molecules comprising one or more specific sequences in a sample containing different species of nucleic acid molecules, the said method comprising the steps of:

a) denaturing the said double-stranded nucleic acid molecules in the sample by applying a physical force to the said molecules;
b) providing one or more single-stranded nucleic acid molecules corresponding to the said one or more sequences;
c) renaturing the said denatured double-stranded nucleic acid molecules of step a) in the presence of the said single-stranded nucleic acid molecule;
d) detecting the double-stranded nucleic acid molecules where renaturation is blocked by the said one or more single-stranded nucleic acid molecules; and
f) numerating the molecules of step d).

Preferably, at least 2 single-stranded molecules are provided at step b), more preferably, at least 3, still more preferably, at least 5, even more preferably, at least 10, most preferably at least 15.

The present invention can thus be used every time there is a need to quantify nucleic acid sequences. Applications include the fields of in vitro diagnostics, including clinical diagnostics, research in the fields of molecular biology, high throughput drug screening, veterinary diagnostics, agricultural-genetics testing, environmental testing, food testing, industrial process monitoring, biosecurity, forensics, and insurance testing. In vitro diagnostics and clinical diagnostics is related to the analysis of nucleic acid samples drawn from the body to detect the existence of a disease or condition, its stage of development and/or severity, and the patient's response to treatment. In high throughput drug screening and development nucleic acids are used similarly to other agents, such as, antigens, antibodies, receptors, etc., to analyze the response of biological systems upon exposure to libraries of compounds in a high sample number setting to identify drug leads. Veterinary diagnostics and agricultural genetics testing involve samples from a non-human animal or a plant species similar to in vitro diagnostics and to provide means of quality control for agricultural genetic products and processes. In environmental testing, organisms and their toxins that indicate the pollution of an environmental medium, e.g. soil, water, air, etc., are analyzed. Food testing includes the quantitation of organisms, e.g. bacteria, fungi, etc., as a means of quality control. In industrial process monitoring, nucleic acids are detected and/or quantified to indicate proper control of a production process and/or to generate a signal if such processes are out of control. In insurance testing organisms and/or their toxins are identified in screening tests to determine the risk category of a client or to help approve candidates. There are various other applications of the detection and/or quantitation of nucleic acids and new applications are being developed constantly.

One of these applications is the analysis of gene expression. Numerous methods for analyzing gene expression have been described in the art. However, the most commonly used methods such as RT-PCR and DNA-microarrays use fluorescent nucleotides, which may be expensive. In addition, prior PCR amplification is required in order to obtain the desired sensitivity. By comparison, the present invention provides a method for measuring gene expression at the single-molecule level, with no amplification or fluorescent nucleotide required.

Thus, in a first embodiment, the present invention relates to a method for measuring the expression of a gene in a sample. By "expression of a gene", it is herein referred to the transcription of the said gene, i.e. the synthesis of a messenger RNA (mRNA) molecule by an RNA polymerase from the gene DNA template; "measuring the expression of a gene" as used herein means measuring the quantity of the specific mRNA molecule corresponding to the said gene.

According to this embodiment, the quantity of the said mRNA corresponding to the said gene is thus measured by one of the quantification methods described above.

It will be immediately apparent to the skilled person that the said quantification method is advantageously performed on double-stranded nucleic acid molecules. Preferably, in a first step, a double-stranded nucleic acid molecule is obtained by replication of the RNA transcript. Thus, according to this embodiment, the present invention provides a method for measuring the expression of a gene in a sample, comprising the steps of:

a) synthesizing double-stranded nucleic acid molecules by replication of the RNA molecules present in the sample, and
b) quantifying the mRNA molecule species corresponding to the said gene by one of the methods described above.

A number of enzymes are known which use single-stranded RNA as a template to make a double-stranded nucleic acid. For example, double-stranded RNA molecules can be obtained by the action of a RNA-dependent RNA polymerase. Preferably, the said transcripts are first retrotranscribed into cDNA by the reverse transcriptase enzyme. The skilled person will realize that retrotranscription has several advantages. For example, it can be initiated from a poly-T oligonucleotide which is already anchored to a solid surface. Moreover, the resulting RNA/cDNA hybrid can be treated first with an RNase, and then with a DNA polymerase, leading to degradation of the RNA moiety and synthesis of a new complementary DNA strand. Advantageously, a hairpin sequence is ligated at the free end of the cDNA strand and can be used as a primer for the synthesis of the new DNA strand.

In another embodiment, the invention relates to a method for determining chromosomal abnormalities. By "chromosomal abnormality", it is herein referred to an atypical number of chromosomes or a structural abnormality in one or more chromosomes. An atypical number of chromosomes is called "aneuploidy": it is thus the condition of having less than or more than the normal diploid number of chromosomes. Aneuploidy occurs when an individual is missing either a chromosome from a pair (monosomy) or has more than two chromosomes of a pair. A "trisomy" is an aneuploidy in which there are three copies, instead of the normal two, of a particular chromosome. By "structural abnormality in a chromosome", it is herein meant an event affecting the copy number of a portion of a chromosome, such as e.g. a deletion, a translocation, a duplication, a ring, etc.

Such chromosomal abnormalities occur during cell division, when either whole or parts of chromosomes fail to separate properly. For example, as cancerous cells progress through oncogenesis, they accumulate chromosomal abnormalities, such as deletions, translocations, gains or loss of entire chromosomes. These chromosomal abnormalities are thought to be linked to the acquisition of the cancerous phenotype and are specific for each cancer type. The more advanced the cancer, the greater number of chromosomal abnormalities. Detecting such chromosomal abnormalities is thus usually very informative about the tumor aggressiveness and the prognosis of the patient.

In this embodiment, the invention thus provides a method for detecting an abnormal distribution of a specified chromosome portion in a biological sample from a subject. More specifically, the said method comprises the steps of:
  a) quantifying the level of the said specified chromosome portion by one of the methods described above,
  b) quantifying the level of another chromosome portion by the method described above,
  c) calculating the ratio between the level obtained in a) and the level obtained in b), and
  d) determining whether the said specified chromosome portion is abnormally distributed.

As explained above, cancer cells accumulate chromosome abnormalities as they progress through the different stages of oncogenesis. Thus the detection of an abnormal distribution of a chromosome in tumor cells is an indication of the aggressiveness of the said tumor: the more chromosome portions abnormally distributed, the more aggressive the tumor.

According to a preferred embodiment, the subject of the invention is thus a cancer-suffering patient. In this embodiment, the invention provides a method for diagnosing cancer aggressiveness in a cancer sample of a cancer-suffering patient, said method comprising the steps of:
  a) quantifying the level of a first specified chromosome portion in said patient cancer sample,
  b) quantifying the level of a second chromosome portion in said patient cancer sample,
  c) calculating the ratio between the level obtained in a) and the level obtained in b),
  d) determining whether the said specified chromosome portion is abnormally distributed, and
  e) diagnosing aggressiveness if the said chromosome portion is abnormally distributed.

A "chromosome portion" according to the invention refers to either an entire chromosome or a significant fragment of a chromosome. For example, moderate Down syndrome has been associated with partial trisomy 21q22.2→qter. The present invention thus provides a method for quantifying a chromosome portion which is suspected of abnormal distribution (the chromosome portion of step a) and comparing this quantification with the one of a reference chromosome portion. A "reference chromosome portion" according to the invention is thus a chromosome portion which is known not to be abnormally distributed. In the present embodiments of the invention, the chromosome portion of step b) is a reference chromosome portion.

Of course, it is important that the sequences for quantifying the chromosome portions of steps a) and b) are selected so as to be specific for the corresponding chromosome portions. The person of skills in the art will easily realize that the required information can be obtained from the publicly available sequence databases, such as Genbank.

The population of double-stranded nucleic acid molecules is advantageously obtained by digesting first the chromosomes by a rare-cutter restriction enzyme. As known by the person of skills in the art, a rare-cutter restriction enzyme is a restriction enzyme with a recognition sequence which occurs only rarely in a genome, for example a recognition sequence comprising 7 or 8 bases. Examples of such rare-cutter enzymes include SfiI, Xma I, Asc I, AsiS I (isoschizomer Sgf I), Not I (isoschizomer CciN I), Sbf I (isoschizomers Sse8387 I, Sda I), Fse I, Pac I etc. All these enzymes are commercially available. In a second step, the restriction fragments thus obtained are digested with a common, 6-base restriction enzyme, such as EcoRI, BamHI, XhoI, etc. The resulting linear double-stranded fragments can then be transformed into hairpins. Techniques allowing the free ends of double-stranded to be joined together are known and some are described in greater details in what follows.

Fetal aneuploidy is usually the result of a chromosome segregation defect during meiosis in the parental germ line. Although, fetal aneuploidy is not as common as other birth defects, affecting 9 in 1000 births, its detection has offered considerable technical challenges.

Maternal blood contains free maternal DNA and free fetal DNA, said fetal DNA ending up in the blood as a result of cellular death, shear etc. (Herzenberg et al., *Proc. Natl. Acad. Sci. USA*, 76: 1453-1455, 1979; Bianchi et al., *Proc. Natl. Acad. Sci. USA*, 87: 3279-3283, 1990). It is known that cell-free fetal DNA represents only 3-6% of the DNA that is present in the maternal plasma (Lo et al., *Am J Hum Genet*, 62: 768-775, 1998). Methods have been described for diagnosing fetal aneuploidy from maternal blood; however, these methods require a step of amplification of the genetic material or use shotgun sequencing, a method with prior PCR-based enrichment (Lo, *BJOG*, 116: 152-157, 2009; Fan et al., *Proc. Natl. Acad. Sci. USA*, 105(42): 16266-16271, 2008; Chiu et al., *BMJ*, 342: c7401, 2011 doi: 10.1136/bmj.c7401), and are thus susceptible of potential bias.

In another preferred embodiment, the said subject is thus a pregnant mother. According to this embodiment, the invention provides a method for diagnosing a fetal aneuploidy from a blood sample of said pregnant mother, comprising:
  a) quantifying the level of a first specified chromosome portion in said blood sample,
  b) quantifying the level of a second chromosome portion in said blood sample,
  c) calculating the ratio between the level obtained in a) and the level obtained in b),
  d) determining whether the said specified chromosome portion is abnormally distributed, and
  e) diagnosing fetal aneuploidy if the said chromosome portion is abnormally distributed.

Preferably, the said specified chromosome portion is a chromosome portion which is suspected of being abnormally distributed in the fetus. Advantageously, the second chromosome portion is a reference chromosome portion, i.e. a chromosome portion which is not affected by an abnormal distribution; the said second chromosome portion is thus preferably disomic in fetal cells.

Preferred fetal chromosomal aneuploidies and accompanying diseases or disorders which can be determined by the method of the present invention include Turner syndrome (gonosomal monosomy), Klinefelter syndrome (XXY gonosomes), triple-X syndrome (XXX gonosomes), Down syndrome (Trisomy 21), Edwards syndrome (Trisomy 18) or Patau syndrome (Trisomy 13). Uniparenteral disomy is known for chromosome 15 as Prader-Willi-Syndrome. If such a uniparenteral disomy is to be detected, the DNA must also be analysed in a way which distinguishes whether it is of maternal or paternal inheritance. Unbalanced translocations as used herein encompass, preferably, unbalanced Robertson trisomy, rob(13q;14q). Other structural aberrations which can be preferably determined by the method of the invention include 4q-deletion (Wolf-Hirschhorn syndrome), 5q-deletion (cri du chat syndrome) or microdeletion syndromes, in particular, 17ql1 0.2 deletion (Smith-Magenis syndrome) or 22ql 1.2 deletion (DiGeorge syndrome).

In a preferred embodiment, the sequence used in steps a) and b) are sequences specific for fetal DNA. For example, the said sequences correspond to the alleles inherited from the father. In another embodiment, neither sequence is specific for either fetal or maternal DNA. However, since 10% of the DNA present in the blood is of fetal origin, a trisomy should result in a ratio of step c) of 1.05. About 1 million beads would have to be probed (by scanning the sample) corresponding for each chromosome to an average $2\times10^4$ sequences of which about $2\times10^3$ will be of fetal origin. The expected statistical (counting) error will be about 1% which allows for large enough S/N for diagnostics.

Implementation of the method of the invention has been made possible, in particular, by the existence of devices designed for probing real-time nucleic acid interaction at the single-molecule level. Such a device is described for example in U.S. Pat. Nos. 7,052,650 and 7,244,391. The apparatus described therein uses magnetic traps to apply a picoNewton scale force on a micron-sized superparamagnetic bead. Briefly, the said apparatus comprises an optical microscope, magnets and a PC. The double-stranded nucleic acid molecules are anchored at multiple points at one end to a motionless element, e.g. a surface, and at the other end to a movable surface, in this case a magnetic bead. Magnets are provided for acting on the bead. In particular, the magnets may be used for pulling the bead away from the surface. However, the implementation of the method of the invention is not restricted to the above apparatus. Any device which allows one to fully extend and then refold a molecule of double stranded nucleic acid, whilst monitoring at the same time the extension of the said molecule can be used to implement the method of the invention. For example, optical tweezers may be used; they require however prior force calibration and are not easily parallelized for high throughput measurements. Further drawbacks are the lack of total torsional control of the nucleic acid and, the possible local heating of the solution by the focussed laser which may alter the hybridization conditions.

The double stranded nucleic acid is incubated for a few minutes in a solution of adequate beads (for example streptavidin coated ones) to which it binds by one of its labeled (for example biotin) ends. The beads can be transparent if optical tweezers are later used for manipulation or magnetic if one uses magnetic traps or tweezers for manipulation.

The bead-nucleic acid assembly is injected in a fluidic chamber the surface of which has been treated such as to bind the other labeled end of the molecule (for example a surface coated with anti-Dig to bind the Dig-labeled end of the nucleic acid). The beads are thus anchored to the surface via a nucleic acid hairpin, see FIG. 1a. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the nucleic acid molecule anchoring the beads to the surface various techniques have been described. One can use the light of a focused laser beam to trap a transparent bead near the focal point. By the relative translation of the beam with respect to the anchoring surface one can apply a force on the tethering molecule (a typical optical tweezers assay). The exerted force being proportional to the displacement of the bead from its equilibrium position, to exert a constant force on the tethering molecule requires a feedback loop on the trapping beam.

To exert a constant force on a bead, the use of the hydrodynamic drag generated by a flow around the bead has been described, but it usually yields a low spatial accuracy (>100 nm). The preferred embodiment uses a magnetic trap to pull on super-paramagnetic beads anchored to a surface by a nucleic acid hairpin as described above. In this configuration, small magnets placed above the sample are used to apply a constant force on the anchored bead, whose position can be determined with <1 nm accuracy (depending on the pulling force and the dissipation due to hydrodynamic drag)

In every case one notices that the tethering hairpin can be mechanically fully unzipped by pulling on the beads with a force larger than about 16 pN. Reducing the tension on the molecule to below about 11 pN allows the hairpin to re-zip spontaneously (the unzipping transition is reversible though hysteretic). If, during the unzipped phase, some molecules in solution (such as proteins or complementary oligonucleotides of DNA, RNA, LNA or PNA) have bound to the stretched single stranded nucleic acid, these molecules will block the rezipping of the hairpin when the force is lowered to below 11 pN. The principle of the assay is thus to switch between two forces: a large one $F_{open}$ to open the hairpin and a smaller one $F_{test}$ used to allow re-zipping and to measure the extension of the molecule at transient blockages. The blocking position is related to the sequence by a linear relation between full extension and the blocked one. For best accuracy, the full extension is preferably measured at the test force $F_{test}$. This is achieved by designing the hairpin loop such that it requires a fraction of a second to refold once the force is reduced from $F_{open}$ to $F_{test}$.

In order to attach nucleic acids to surfaces or supports, use may be made of any one of the techniques known in the field. Essentially, the nucleic acid becomes anchored directly to the support, for example the micro-bead, which involves a functionalization of this surface, for example by coating it with streptavidin, a COOH group, and the like, capable of reacting with the functionalized end of the nucleic acid.

Such methods necessitate, in general, functionalizing the nucleic acid, especially the 3' and 5' ends, that is to say grafting appropriate chemical groups onto them. It is, moreover, preferable to join the other two free ends of the molecule by a loop in order to prevent the strands from dissociating at the end of the operation, so that the latter can be repeated if appropriate. For this purpose, different procedures may be adopted.

The simplest is to functionalize, using synthetic oligonucleotides, one of the ends of a double-stranded nucleic acid with two different functions (biotin and amine, for example), which permit anchoring to two different pretreated surfaces. The two strands at the other end may be joined using a partially paired synthetic nucleotide in the form of a loop. In this way, a paired, single-stranded nucleic acid, i.e. a hairpin, is produced from a double-stranded nucleic acid. The advantage of this method lies in its capacity to functionalize a heterogeneous population of large nucleic acid fragments (as are obtained by fractionation of a gene or chromosome), which can then be analyzed simultaneously. In this case, the nucleic acid sample is fractionated using two (or more) restriction enzymes, which enables a subpopulation to be obtained with two different restriction sites at its ends which are similar over all the fragments. This enables the two ends to be treated differently (for example by joining one end to an oligonucleotide in the form of a loop possessing the appropriate restriction site at its end). The drawback of this method lies in the steric interference between the two adjacent functional groups, which can make coupling to the surfaces difficult. To solve this problem, it can be advantageous to add at each free end of the hairpin molecule a "spacer" sequence of bases, to the end of which a functional group is then added; the two spacer sequences are non-complementary, affording each functional group enough space to bind to its dedicated surface. More advantageously, the sequence of each spacer sequence is designed in order to use single-stranded sequencing primers of known sequence in the sequencing method of the invention. The addition of a loop and/or spacers to the double-stranded nucleic acid molecules can be performed with any of the methods commonly used in molecular biology. These methods are well known to the person skilled in the art and there is thus no need to detail them here.

As regards the actual anchoring techniques, there are many of these and they derive from the techniques for anchoring macromolecules (proteins, DNA, and the like) to commercially available pretreated surfaces. Most of these techniques have been developed for immunology tests, and link proteins (immunoglobulins) to surfaces carrying groups (—COOH, —NH$_2$, —OH, and the like) capable of reacting with the carboxyl (—COOH) or amine (—NH$_2$) ends of proteins.

The covalent anchoring of nucleic acid may be accomplished directly, via the free phosphate of the 5' end of the molecule, which reacts with a secondary amine (Covalink —NH surface marketed by Polylabo at Strasbourg) to form a covalent bond. It is also possible to functionalize DNA with an amine group and then to proceed as with a protein.

There are also surfaces coated with streptavidin (Dynal beads, and the like), which permit quasi-covalent anchoring between the streptavidin and a biotinylated DNA molecule. Lastly, by grafting an antibody directed against digoxigenin onto a surface (by the methods mentioned above), a nucleic acid functionalized with digoxigenin may be anchored thereto. This represents merely a sample of the many possible anchoring techniques.

Among the attachment and anchoring techniques, there should also be mentioned, for example, the techniques described in Patent EP 152 886 using an enzymatic coupling for the attachment of DNA to a solid support such as cellulose.

Patent EP 146 815 also describes various methods of attachment of DNA to a support.

Similarly, patent application WO 92/16659 proposes a method using a polymer to attach DNA.

Naturally, the nucleic acid may be attached directly to the support but, where necessary, especially with a view to limiting the influence of the surfaces, the nucleic acid may be attached at the end of an inert arm of peptide or other nature, as is, for example, described in European patent EP 329 198.

The examples below will enable other features and advantages of the present invention to be brought out.

FIGURE LEGENDS

FIG. 1. Detection of oligonucleotide-induced blockages during rehybridization. (a) Hairpin construction design with pre-planted target in the stem. (b) Example of roadblocks due to the hybridization of two oligonucleotides (SEQ ID NO. 1: 5'-ACAGCCAGC-3', SEQ ID NO. 2: 5'-ATGACAATCAG-3') on the 83 bps hairpin (see Methods). Left panel: Experimental traces recorded at $F_{open}$=17.8 pN (orange) and $F_{test}$=11.4 pN (blue; see force trace at the top). Five different extension levels are observed corresponding from top to bottom to: (i) the open hairpin at $F_{open}$, (ii) the open hairpin at $F_{test}$, (iii) the partially annealed hairpin blocked by the first oligo, (iv) the partially annealed hairpin blocked by the second oligo and (v) the folded hairpin. The black curve corresponds to a 1 s average of the raw data. Right panel: Histogram of blockages (ii)-(iv). The black curve represents the histogram of the number of blockages per cycle at a given extension of the hairpin upon rehybridization at Ftest: $\Delta Z = Z_{block} - Z_{close}$ in base pairs obtained from ~23 force cycles on a single hairpin. Gaussian fits to the data are shown in red. The variance of these fits ($\sigma$ ~1 nm) defines the resolution of the apparatus. The roadblocks $Z_{block1}$ and $Z_{block2}$ are observed at 39.60 and 28.66 bps along the hairpin, in good agreement with the expected position of 40 and 29 bps (shown in green).

Figure 2:
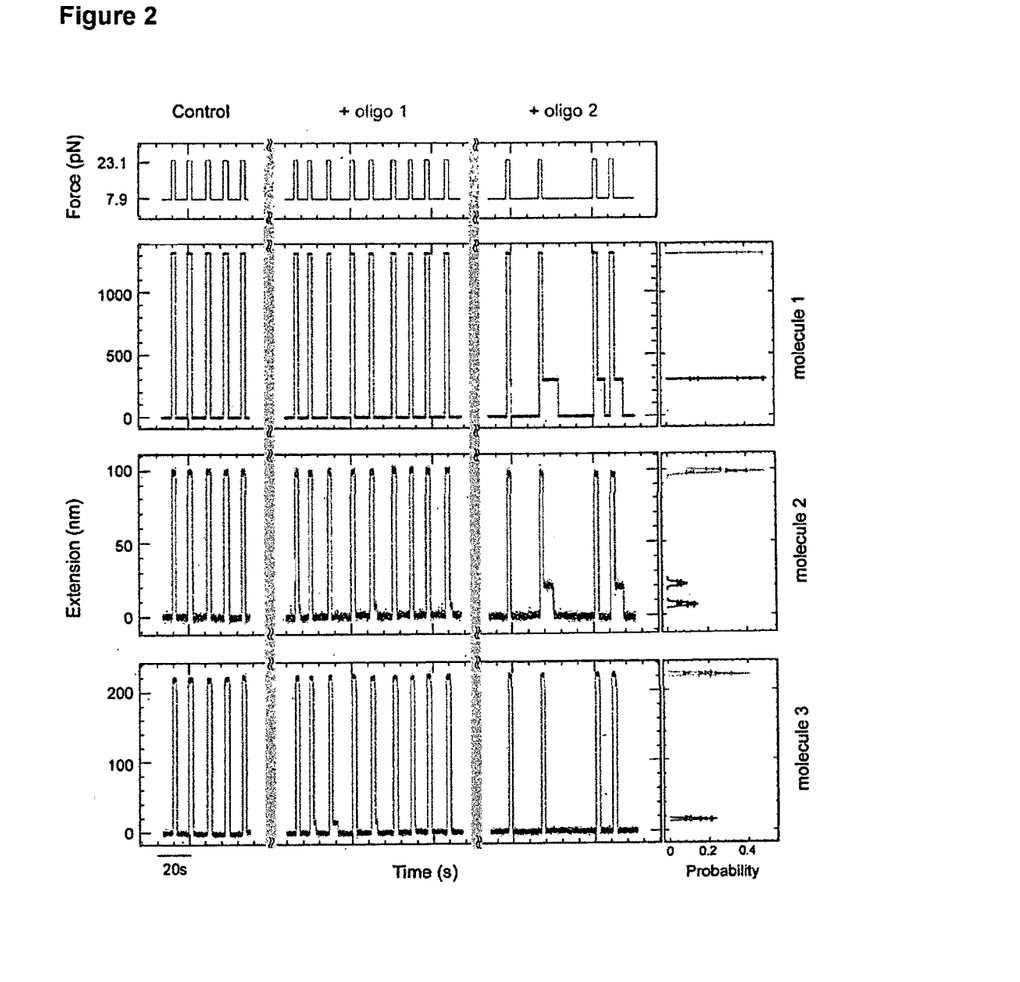

FIG. 2. Sequence identification by hybridization. Three different hairpins (marked as molecule 1, 2, 3) were identified by two different oligos (marked as oligo1 and 2) (see Methods). Left panel: Experimental traces recorded during hairpin open-close cycles. To show the corresponding blockage, oligos 1 and 2 were added sequentially into the solution: oligo 1 hybridized on molecules 2 and 3, while oligo 2 hybridized on molecules 1 and 2. Right panel: Histogram of blockages from oligos 1 (orange) and 2 (blue) on each molecule, while the full extension of the molecule is shaded in grey.

Figure 3:
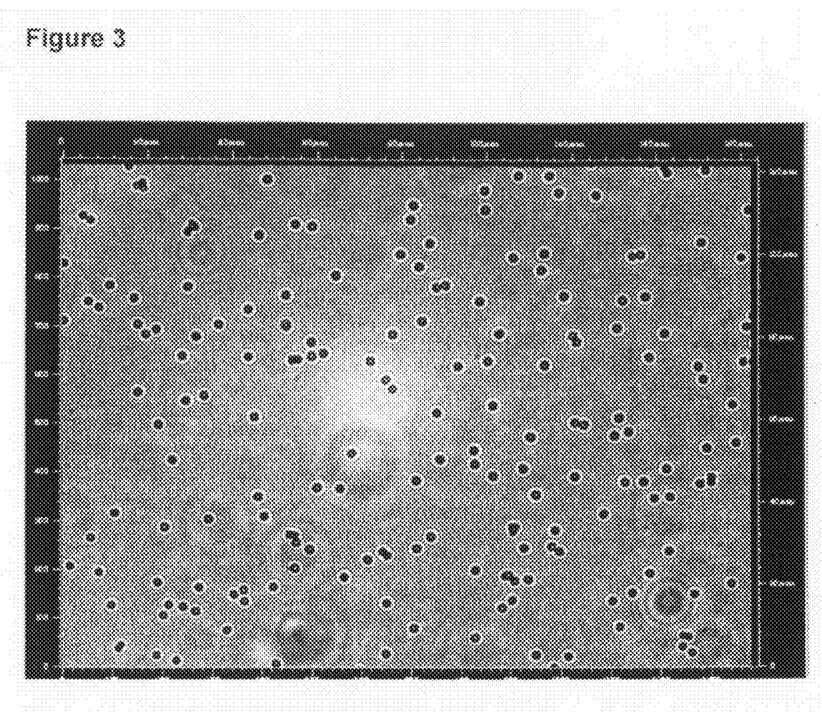

FIG. 3. Field of view of the camera showing many beads attached by a single hairpin to a glass surface. They are visualized by microscopy using parallel illumination from a bright red LED. The small diffraction rings surrounding the beads are used to measure their vertical position FIG. 4. Scheme showing the hairpin design.

Figure 5:
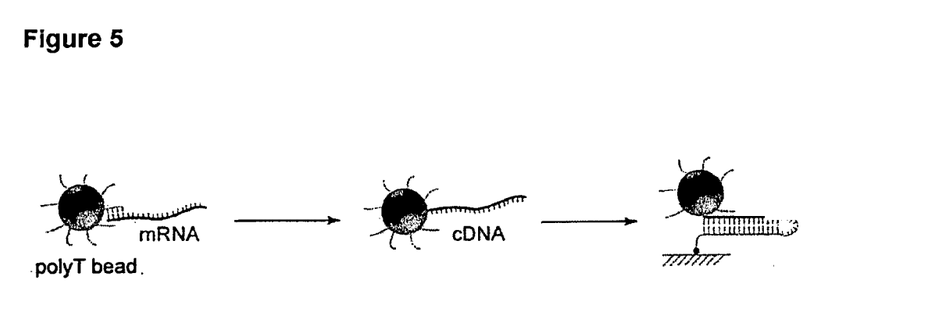

FIG. 5. The scheme for generating a cDNA hairpin structure from mRNA.

EXAMPLES

Methods

DNA Hairpin Construction

Figure 4:
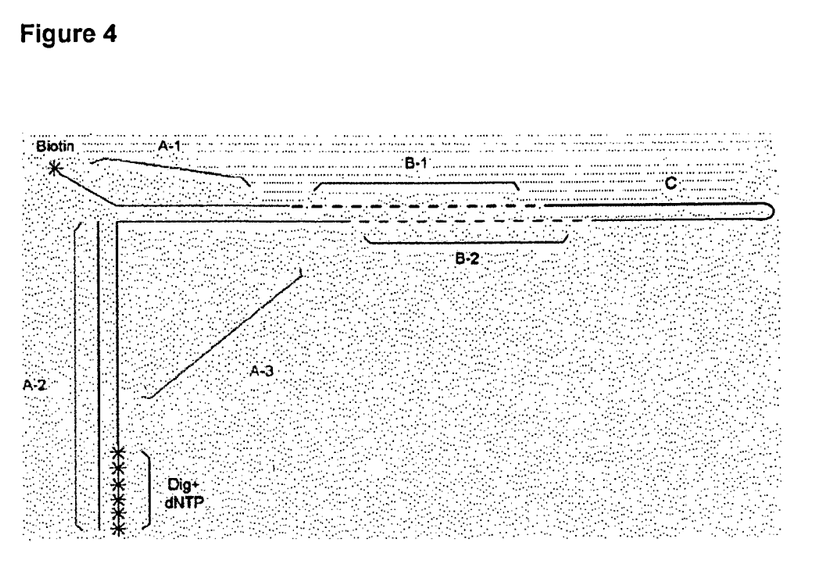

Short DNA hairpins (83 bps in FIGS. 1 and 2, or 179 bps in FIG. 2) were constructed by ligating three separate synthetic oligonucleotides (Eurogentec and Integrated DNA technology) as shown in FIG. 4. In the first step, oligo A-1 (SEQ ID NO. 3: 5'-biotin-TTT TTT TTT TTT TTT TTT TTT TTT TTT TTT TTT TTT TTT TTT TTT TTT TTG GAT TCG CGG GTC TCT-3') and oligo A-2 (SEQ ID NO. 4: 5'-AAC CGT CCT TTA CTT GTC ATG CGC TCT AAT CTC TGG GCA TCT GGC TAT GAT GTT GAT GGA ACT GAC CAA ACG TCG GTG GG-3') were annealed to the complementary oligo A-3 (SEQ ID NO. 5: 5'-phosphorylated-AGG AAG AGA CCC GCG AAT CCC CCA CCG ACG TTT GGT CAG TT-3') in dH$_2$O by heating to 95° C. for 5 min, then rapidly cooling to 80° C., followed by a slow decrease of 0.7° C. every 10 s until reaching 4° C. These annealed products, marked part A, were cleaned up with NucleoSpin Extract II kits (Clontech). We repeated the annealing and clean up procedure for oligo B-1 (SEQ ID N.O. 6: 5'-phosphorylated-TCC TGA TTG TCA TCG GCT GGC TGT TCG GTT AGT TTC GAA GAC TT-3') and oligo B-2 (SEQ ID NO. 7: 5'-phosphorylated-GCG AAA GTC TTC GAA ACT AAC CGA ACA GCC AGC CGA TGA CAA TC-3'), which correspond to the middle section of the 83 bps hairpin, or oligo B'-1 (SEQ ID NO. 8: 5'-phosphorylated-TCC TCG TGC GTG AGC GAG CGC GGT CGG TCG GTC GGT AGC GAG CGC GTG CGT GCG TGC GTG GGC TGG CTG GCT GGC TCG GTC GGT CGT GCG TGC GGT CGG TGG CTG GCT AGC GAG CGA GCG AGC GGG CTG GCT GM GAC TT-3') and oligo B'-2 (SEQ ID NO. 9: 5'-phosphorylated-GCG AAA GTC TTC AGC CAG CCC GCT CGC TCG CTC GCT AGC CAG CCA CCG ACC GCA CGC ACG ACC GAC CGA GCC AGC CAG CCA GCC CAC GCA CGC ACG CAC GCG CTC GCT ACC GAC CGA CCG ACC GCG CTC GCT CAC GCA CG-3'), which correspond to the middle section of the 179 bps hairpin. These annealed products are marked part B or B' or B". We ligated part A, part B (or part B', B") to oligo C (SEQ ID NO. 10: 5'-phosphorylated-TCG CGC CTG ATC GTC CAC TTT TTT TTT AGT GGA CGA TCA GGC-3'), which is the loop of hairpin, using T4 ligase (5 U/µl, Fermentas) in the 1×T4 ligase reaction buffer at 25° C. for 1.5 h, then stopped the reaction by heating to 65° C. for 20 min. The ligation mixture was cleaned up with Nucleo-Spin Extract II kits. Finally, the digoxigenin labels were added by a fill-in reaction using Klenow (3→5' exo–) (New England Biolabs) in the 1×NEB2 buffer with 1 mM digoxigenin-dUTP (Roche) at 37° C. for 15 min, and stopped by heating to 75° C. for 20 min. The hairpin products were cleaned up with NucleoSpin Extract II kits again.

The preparation method for the 1241 bps hairpin (FIG. 2) is described in Manosas et al. (*Nat. Chem. Biol.* 5: 904-912, 2009).

Single-Molecule Assay

The constructed hairpin, labeled at one end with digoxigenin and biotin at the other, was attached to the glass surface of a microscope flow chamber previously coated with anti-digoxigenin and passivated with bovine serum albumin (BSA), and to a 1 µm super-paramagnetic bead coated with streptavidin (DYNAL MyOne). Small magnets were used to pull on single DNA molecules attached to the beads. The acquisition of the molecule's extension Z(t) is done with a CCD camera at 31 Hz. The raw data are averaged over 1 s, achieving a resolution of ~1 nm, while the stretching force, F, is measured with 10% accuracy. During data collection we subtract the vertical position of reference beads stuck to the surface ($Z_{ref}$) from the vertical position traces Z(t), which helps to reduce set-up drift. For every opening/closing cycle, we take the center ($<Z_{close}>$) of a Gaussian fit to $Z_{close}$ ($F_{test}$) as the reference position of the closed hairpin (extension 0 nm). Similar Gaussian fits are used to determine the average position in one cycle of $Z_{open}$ ($F_{test}$) and $Z_{block}$($F_{test}$). The error bars represent the s.e.m.

For the hybridization identification in FIG. 2, molecule 1 is the 1214 bps hairpin, molecule 2 is the 83 bps hairpin, and molecule 3 is the 179 bps hairpin, while oligo 1 is SEQ ID NO. 11: 5'-GAAGAGACCC-3' and oligo 2 is SEQ ID NO. 12: 5'-CAGCCGATGAC-3'.

Results

Detection of Roadblocks in the Rezipping Pathway of a Hairpin

In the present approach a DNA hairpin is attached at one end to a coverslip via a digoxigenin (Dig)-anti-Dig bond and at the other to a magnetic bead via a biotin-streptavidin bond. This DNA hairpin can be generated in various ways. For example it can be formed by ligation of a genomic DNA fragment to a DNA loop at one end and to a DNA fork structure labeled with biotin and Dig at its other end (FIG. 1a). Alternatively this hairpin can be generated from cDNA obtained after trapping mRNAs on poly-T coated beads and reverse transcription (FIG. 5).

Small magnets in the vicinity of the sample are used to apply a vertical force on the tethered beads. The distance of a bead to the surface (i.e. the end-to-end distance of the hairpin) can be deduced in real time from the bead's image (Gosse & Croquette, *Biophys. J.*, 82: 3314-3329, 2002). Alternatively, it can be deduced using evanescent field illumination from the intensity of the light scattered by the bead. While the set-up is similar to the DNA unzipping experiment performed with optical tweezers (Brower-Toland et al., *Proc. Natl. Acad. Sci. USA*, 99: 1960-1965, 2002), the use of a magnetic trap allows for a high degree of parallelism through the simultaneous application of the same force on many molecules (Gosse & Croquette, *Biophys. J.*, 82: 3314-3329, 2002; Stick et al., *Science*, 271: 1835-1837, 1996).

We modulate the force to periodically open and close the DNA hairpins in a solution (Essevaz-Roulet et al., *Proc. Natl. Acad. Sci. USA* 94: 11935-11940, 1997). containing oligonucleotides complementary to a section of the hairpin. In FIG. 1b an 83 bps hairpin is periodically unfolded by applying a force $F_{open}$ (>15 pN) and rezipped by reducing the force to $F_{test}$ (~10 pN). In the unfolded or opened state two different oligonucleotides in solution can hybridize to their individual complementary sequences on the hairpin. They transiently block the refolding of the hairpin at low force, which are readily observable as two pauses in the hairpin's extension in the time course of its refolding.

This measurement scheme provides two pieces of valuable information: the position and lifetime of the blockage along the hairpin. The opening of one base pair results in a change in the hairpin extension of about 0.85 nm. With the present resolution of our apparatus (~1 nm), we can thus record the position of a blockage with an accuracy of about one nucleotide. Notice that switching between the opened and closed states of the hairpin provides a differential extension measurement which is insensitive to slow experimental drifts. Moreover the precise value of the applied force is not critical as long as it remains constant.

Concerning the blockage lifetime, which is related to the stability of the hybrid, we found that it depends on the applied tension, the size of the complementary oligonucleotide and the presence and location of mismatches between the oligonucleotide and the hairpin (data not shown).

Sequence Identification by Hybridization Fingerprinting or Single Cycle Ligation The identification of a desired DNA in a given sample is a relevant issue in many situations, such as the detection of genetic mutations, gene duplications, mRNA expression patterns, etc. With the present scheme this identification issue is quite easy. It requires the detection of a given hybridization fingerprint obtained with a set of chosen short (~10 nt) oligonucleotides on a DNA hairpin sample. This can be achieved by testing for blockages during rehybridization of the hairpins in the presence of one or a few probe oligonucleotide(s). As shown in FIG. 2 the identification of three different DNA sequences can be achieved by hybridization of two different oligonucleotides. Notice that since we can detect the exact position of the hybrid it is not necessary to test each probe sequentially as is usually done. Rather one may identify the blockage positions along the hairpin of several selected probes and use this hybridization pattern, instead of the mere presence of hybrids, as a fingerprint of the DNA sequence.

The invention claimed is:

1. A method for quantitating nucleic acid hairpin molecules whose renaturations are blocked by single-stranded nucleic acid molecules comprising:
   a) providing a sample containing nucleic acid hairpin molecules, each of the nucleic acid hairpin molecules consisting of a double-stranded stem and a single-stranded loop,
      wherein the 5' and 3' ends of each of the nucleic acid hairpin molecules are bound to different surfaces respectively, and wherein one of the surfaces bound to each of the nucleic acid hairpin molecules is a movable bead and another of the surfaces bound to each of the nucleic acid hairpin molecules is a fixed surface;
   b) applying a force to the movable bead such that the movable bead is moved away from the fixed surface, thereby yielding completely denatured hairpin molecules;
   c) providing the single-stranded nucleic acid molecules complementary to the completely denatured hairpin molecules;
   d) reducing the force applied to the movable bead to allow renaturation of the completely denatured hairpin molecules in the presence of the single-stranded nucleic acid molecules; and
   e) detecting blockage of the renaturation of the hairpin molecules due to hybridization of the single-stranded nucleic acid molecules to the completely denatured hairpin molecules during step d); and
   f) quantitating the number of the nucleic acid hairpin molecules whose renaturations are blocked by the single-stranded nucleic acid molecules.

2. The method of claim 1, wherein all of the single-stranded nucleic acid molecules have the same nucleotide sequence.

3. The method of claim 1, wherein the single-stranded nucleic acid molecules consist of 2 or more different nucleotide sequences.

4. The method of claim 1, wherein the single-stranded nucleic acid molecules are 10-50 nucleotides in length.

5. The method of claim 1, wherein the single-stranded nucleic acid molecules are 10-30 nucleotides in length.

6. The method of claim 1, wherein the single-stranded nucleic acid molecules are 10-20 nucleotides in length.

7. The method of claim 1, wherein the single-stranded nucleic acid molecules are 10-12 nucleotides in length.

8. The method of claim 1, wherein steps a)-e) are repeated.

9. The method of claim 1, wherein the force is reduced to less than or equal to 12 pN in step d).

10. The method of claim 1, wherein the force is reduced to less than or equal to 11 pN in step d).

11. The method of claim 1, wherein the force is reduced to less than or equal to 10 pN in step d).

12. The method of claim 1, further comprising measuring the duration of the blockage in step e).

13. The method of claim 1, wherein the nucleic acid hairpin molecules are made by replicating RNA molecules.

14. The method of claim 1, wherein the movable bead is a magnetic bead.

15. The method of claim 14, wherein the force is a magnetic force.

* * * * *

SEQUENCE LISTING

<160> NUMBER OF SEQ ID NOS: 12

<210> SEQ ID NO 1
<211> LENGTH: 9
<212> TYPE: DNA
<213> ORGANISM: Artificial Sequence
<220> FEATURE:
<223> OTHER INFORMATION: Oligonucleotide

<400> SEQUENCE: 1 acagccagc                                                                 9

<210> SEQ ID NO 2
<211> LENGTH: 11
<212> TYPE: DNA
<213> ORGANISM: Artificial Sequence
<220> FEATURE:
<223> OTHER INFORMATION: Oligonucleotide

<400> SEQUENCE: 2
atgacaatca g                                                             11

<210> SEQ ID NO 3
<211> LENGTH: 66
<212> TYPE: DNA
<213> ORGANISM: Artificial Sequence
<220> FEATURE:
<223> OTHER INFORMATION: oligonucleotide A-1
<220> FEATURE:
<221> NAME/KEY: misc_binding
<222> LOCATION: (1)..(1)
<223> OTHER INFORMATION: 5'-Biotinylation

<400> SEQUENCE: 3
tttttttttt tttttttttt tttttttttt tttttttttt tttttttttt ggattcgcgg        60
gtctct                                                                   66

<210> SEQ ID NO 4
<211> LENGTH: 80
<212> TYPE: DNA
<213> ORGANISM: Artificial Sequence
<220> FEATURE:
<223> OTHER INFORMATION: oligonucleotide A-2

<400> SEQUENCE: 4
aaccgtcctt tacttgtcat gcgctctaat ctctgggcat ctggctatga tgttgatgga        60
actgaccaaa cgtcggtggg                                                    80

<210> SEQ ID NO 5
<211> LENGTH: 41
<212> TYPE: DNA
<213> ORGANISM: Artificial Sequence
<220> FEATURE:
<223> OTHER INFORMATION: oligonucleotide A-3
<220> FEATURE:
<221> NAME/KEY: misc_feature
<222> LOCATION: (1)..(1)
<223> OTHER INFORMATION: 5'-phosphorylated

<400> SEQUENCE: 5
aggaagagac ccgcgaatcc cccaccgacg tttggtcagt t                            41

<210> SEQ ID NO 6
<211> LENGTH: 44
<212> TYPE: DNA
<213> ORGANISM: Artificial Sequence -continued

```
<220> FEATURE:
<223> OTHER INFORMATION: oligonucleotide B-1
<220> FEATURE:
<221> NAME/KEY: misc_feature
<222> LOCATION: (1)..(1)
<223> OTHER INFORMATION: 5'- phosphorylated

<400> SEQUENCE: 6
tcctgattgt catcggctgg ctgttcggtt agtttcgaag actt            44

<210> SEQ ID NO 7
<211> LENGTH: 44
<212> TYPE: DNA
<213> ORGANISM: Artificial Sequence
<220> FEATURE:
<223> OTHER INFORMATION: oligonucleotide B-2
<220> FEATURE:
<221> NAME/KEY: misc_feature
<223> OTHER INFORMATION: 5'-phosphorylated

<400> SEQUENCE: 7
gcgaaagtct tcgaaactaa ccgaacagcc agccgatgac aatc            44

<210> SEQ ID NO 8
<211> LENGTH: 140
<212> TYPE: DNA
<213> ORGANISM: Artificial Sequence
<220> FEATURE:
<223> OTHER INFORMATION: oligonucleotide B'-1
<220> FEATURE:
<221> NAME/KEY: misc_feature
<222> LOCATION: (1)..(1)
<223> OTHER INFORMATION: 5'-phosphorylated

<400> SEQUENCE: 8
tcctcgtgcg tgagcgagcg cggtcggtcg gtcggtagcg agcgcgtgcg tgcgtgcgtg    60
ggctggctgg ctggctcggt cggtcgtgcg tgcggtcggt ggctggctag cgagcgagcg   120
agcgggctgg ctgaagactt                                               140

<210> SEQ ID NO 9
<211> LENGTH: 140
<212> TYPE: DNA
<213> ORGANISM: Artificial Sequence
<220> FEATURE:
<223> OTHER INFORMATION: oligonucleotide B'-2
<220> FEATURE:
<221> NAME/KEY: misc_feature
<223> OTHER INFORMATION: 5'-phosphorylated

<400> SEQUENCE: 9
gcgaaagtct tcagccagcc cgctcgctcg ctcgctagcc agccaccgac cgcacgcacg    60
accgaccgag ccagccagcc agcccacgca cgcacgcacg cgctcgctac cgaccgaccg   120
accgcgctcg ctcacgcacg                                               140

<210> SEQ ID NO 10
<211> LENGTH: 42
<212> TYPE: DNA
<213> ORGANISM: Artificial Sequence
<220> FEATURE:
<223> OTHER INFORMATION: oligonucleotide C
<220> FEATURE:
<221> NAME/KEY: misc_feature
<222> LOCATION: (1)..(1)
<223> OTHER INFORMATION: 5'-phosphorylated

<400> SEQUENCE: 10
```

-continued

```
tcgcgcctga tcgtccactt tttttttagt ggacgatcag gc                        42

<210> SEQ ID NO 11
<211> LENGTH: 10
<212> TYPE: DNA
<213> ORGANISM: Artificial Sequence
<220> FEATURE:
<223> OTHER INFORMATION: Oligonucleotide

<400> SEQUENCE: 11
gaagagaccc                                                            10

<210> SEQ ID NO 12
<211> LENGTH: 11
<212> TYPE: DNA
<213> ORGANISM: Artificial Sequence
<220> FEATURE:
<223> OTHER INFORMATION: Oligonucleotide

<400> SEQUENCE: 12
cagccgatga c                                                          11
```